United States Patent [19]

Cooke et al.

[11] Patent Number: 4,725,549
[45] Date of Patent: Feb. 16, 1988

[54] HUMAN AND RAT PROLACTIN AND PREPROLACTIN CLONED GENES

[75] Inventors: Nancy E. Cooke; John D. Baxter, both of San Francisco; Joseph A. Martial, Mill Valley, all of Calif.

[73] Assignee: The Regents of the University of California, Berkeley, Calif.

[21] Appl. No.: 592,714

[22] Filed: Mar. 23, 1984

Related U.S. Application Data

[63] Continuation of Ser. No. 189,160, Sep. 22, 1980, abandoned.

[51] Int. Cl.$^4$ .................. C12N 1/00; C12N 15/00; C12N 1/20; C12P 21/00; C12P 21/02; C12P 21/04; C12P 19/34; C12R 1/19; C07H 21/04

[52] U.S. Cl. .................................. 435/243; 435/68; 435/70; 435/71; 435/91; 435/172.1; 435/172.3; 435/253; 435/317; 435/849; 536/27; 935/13; 935/29; 935/73

[58] Field of Search .................. 435/68, 70, 71, 91, 435/172.3, 243, 253, 849, 172.1; 536/27; 935/13, 29, 73

[56] References Cited

U.S. PATENT DOCUMENTS 4,342,832 8/1982 Goeddel et al. .................... 935/13

OTHER PUBLICATIONS

Chang et al, "Phenotypic Expression in E. Coli of a DNA Sequence Coding for Mouse Dihydrofolate Reductase", Nature 275:617 (1978).
Weiss et al, "Importance of Full Size Complementary DNA in Nucleic Acid Hybridization", J. Biol. Chem. 251: 3425 (1976).
McKean et al, "Complete Amino Acid Sequence of the Precursor Region of Rat Prolactin", Biochemistry 17: 5215 (1978).
Gubbins et al, "Construction and Analysis of Recombinant DNAs Containing a Structural Gene for Rat Prolactin", Nucleic Acids Res. 6: 915 (1979).
Nilson et al, "Purification of Pre-Prolactin mRNA from Bovine Anterior Pituitary Glands", J. Biol. Chem. 254: 1516 (1979).
Nilson et al, "Construction and Characterization of a cDNA Clone Containing a Portion of the Bovine Prolactin Sequence", Nucleic Acids Res. 8: 1561 (1980).
Brennessel et al, "Isolation and Characterization of Prolactin-Copy DNA", Biochem. Biophys. Res. Comm. 87: 635 (1979).

*Primary Examiner*—James Martinell
*Attorney, Agent, or Firm*—Ciotti & Murashige Irell & Manella

[57] ABSTRACT

A DNA which comprises a deoxynucleotide sequence coding for prolactin, particularly human prolactin, is described. A transfer vector and an expression vector containing this DNA and microorganisms transformed by these vectors are also described. A method for preparing a reverse transcript (cDNA) from a messenger RNA is also disclosed herein.

The invention described herein was made in the course of, or under, a grant from the National Institutes of Health.

22 Claims, No Drawings

HUMAN AND RAT PROLACTIN AND PREPROLACTIN CLONED GENES

CROSS-REFERENCE TO RELATED APPLICATIONS

This application is a continuation of U.S. application Ser. No. 189,160, filed Sept. 22, 1980 and now abandoned.

BACKGROUND OF THE INVENTION

Prolactin is a polypeptide hormone, synthesized in and secreted by the adenohypophysis (anterior lobe of the pituitary). Prolactin is synthesized as a precursor protein containing an N-terminal signal peptide and the prolactin sequence. The preliminary amino acid sequence for human prolactin has been reported by Shome, B. and Parlow, A. F., *J. Clin. Endocrinol. Metab.*, 45, 1112 (1977). The preliminary amino acid sequence for the N-terminal signal peptide of rat prolactin has been reported by McKean, D. J. and Maurer, R. A., *Biochem.*, 17, 5215 (1978).

Prolactin was first described as being essential for the initiation of lactation in mammals at parturition. In some species, prolactin has been found to also promote milk secretion. In addition, prolactin also initiates secretion of milk in the hypertophied mammary gland. It has been found that prolactin stimulates the synthesis of milk proteins, such as casein and α-lactalbumin. Furthermore, prolactin acts synergistically with estrogen to promote mammary gland proliferation. For a general review of the effects of prolactin see Bern, H. A. and Nicoll, C. S., *Recent Prog. Horm. Res.*, 24, 681 (1968). For a review on the effects of prolactin in man, see Frantz, A. G., et al, *Rec. Prog. Horm. Res.*, 28, 527 (1972).

Prolactin also exhibits an anti-gonadotropic hormone action, that is, prolactin inhibits luteinization by luteinizing hormone and inhibits ovulation induced by pregnant mare's serum. Prolactin induces the secretion of progesterone by the newly formed corpus luteum after ovulation. Progesterone itself inhibits ovulation and it has been noted that the antiovulatory action of prolactin depends on the presence of the corpus luteum. It thus appears that the antiovulatory effect of prolactin may be the result of the prolactin-induced progesterone synthesis by the corpus luteum. For a review of prolactin and human reproduction, see Robyn, C., et al., in *Human Prolactin*, Ed. Pasteels, J. L. and Robyn, C., Americal Elsevier Publishing Co., Inc., New York, p. 167 (1973).

In vitro, prolactin has been found to stimulate glucose uptake and lipogenesis in adipose tissue. When injected, prolactin has been found to mimic a number of actions of growth hormone. Uses of prolactin are based on its known biological activity discussed above. Since prolactin stimulates lactation, it can be administered to insure adequate milk production for breast-feeding mothers. Similarly, rat prolactin, which is very close in amino acid sequence to bovine prolactin, can be administered to dary cows to increase the production of milk. The antiovulatory effect of prolactin can be exploited as a birth control measure by using prolactin as a female contraceptive.

Basic techniques for cloning DNA sequences are now known. For example, Seeburg, P. H. et al, *Nature*, 270, 486 (1977) describes the cloning of the rat growth hormone gene; Shine, J., et al, *Nature*, 270, 494 (1977) describes the cloning of the human chorionic somatomammotropin gene; and Derynck, R., et al, *Nature*, 285, 542 (1980) describes the cloning of the human fibroblast interferon gene.

Methods for the expression of heterologous DNA in a microorganism are now known. In principle, the heterologous DNA coding sequence is inserted in a DNA transfer vector at a point located within an expressible operon. This may result in the production of the desired protein either as such or as a hybrid protein. In the latter case, the inserted sequence must be in reading frame phase with the coding sequence of the operon, and oriented in the same direction with respect to translation. When the conditions are met, translation of the operon results in "read-through" to the inserted coding sequence such that the protein produced is a fusion protein comprising an N-terminal amino acid sequence coded by the expressible operon, followed by an amino acid sequence coded by the insert. See Polisky, B., et al, *Proc. Nat. Acad. Sci. USA*, 73, 3900 (1976); Itakura, K., et al, *Science*, 198, 1056 (1977). Several expressible operons have been employed, including those for β-galactosidase, β-lactamase and tryptophan.

Abbreviations used herein are those abbreviations commonly accepted and used by one of ordinary skill in the art. For example, these abbreviations are acceptable by the *J. Biol. Chem.* without further elucidation.

SUMMARY OF THE INVENTION

The present invention discloses the cloning of a DNA coding for prolactin and the expression of the cloned DNA in microorganisms. The invention is exemplified by the cloning of rat and human prolactin.

mRNA coding for prolactin is isolated from an appropriate source, e.g., adenohypophysis. A reverse transcript (a cDNA copy) is prepared and inserted into a transfer vector. The transfer vector is used to transform bacteria which express the cloned DNA.

A process for preparing a reverse transcript of the mRNA coding for prolactin and useful for other proteins is also disclosed. The process is an improvement on known techniques whereby the entire coding sequence can be duplicated. The improvement comprises tailing the single stranded cDNA (reverse transcript) with dC and priming the formation of the second strand of cDNA (reverse transcript) with a dG oligomer. This improvement prevents the formation of the hairpin loop between the two cDNA strands as currently used in the reverse transcription reactions. Since this loop has to be eliminated before the cloning step, the hairpin loop procedure usually leads to a loss of part of the coding sequence.

BRIEF DESCRIPTION OF THE DRAWINGS

FIG. 1 illustrates the method of preparing the reverse transcript preprolactin cDNA according to the preferred embodiment of the invention;

FIG. 2 sets forth the DNA sequence for rat preprolactin along with the amino acid sequence corresponding thereto.; and FIG. 3 sets forth the DNA sequence for human preprolactin along with the amino acid sequence corresponding thereto.

DETAILED DESCRIPTION OF THE INVENTION

A DNA sequence coding for prolactin is obtained by using the cDNA method. The basic techniques of the cDNA method are known and can be illustrated by Seeburg, P. H., et al, supra and Derynck, R., et al, supra. This method has been modified as discussed below. The cDNA is synthesized by using an RNA preparation preferably enriched in RNA for prolactin, as the template.

The RNA preparation can be obtained from several sources. For example, the RNA can be isolated from the adenohyphophysis (anterior lobe of the pituitary gland) from the desired higher organism, such as rat, bovine or human. The RNA can also be isolated from cultured pituitary cell lines such as the rat GH4 or GC strains and from prolactin secreting adenomas. Preferably, the RNA preparation is enriched in RNA coding for prolactin. Thus, it is preferable to obtain RNA coding for human prolactin from human prolactin secreting adenomas. It is preferable to obtain RNA coding for rat prolactin from pituitaries of rats which have had surgical destruction of the medial basal hypothalamus coupled with estrogen stimulation. The RNA is isolated from any of the above-identified sources using conventional techniques. Polyadenylated RNA is isolated by affinity chromatography. The polyadenylated RNA can be further fractionated by sedimentation through a sucrose gradient. By determining which fraction contains RNA coding for prolactin, it is possible to obtain RNA enriched in the RNA coding for prolactin. This determination is made by performing cell-free translation of the polyadenylated RNA as described by Martial, J. A., et al, *Proc. Nat. Acad. Sci. USA*, 74, 1816 (1977) and analyzing the proteins produced by SDS-acrylamide gel electrophoresis as described by Laemmli, U. K., *Nature*, 227, 680 (1970). The fraction containing preprolactin is further identified by an immune precipitation reaction as described by Martial, J. A., et al, *Proc. Nat. Acad. Sci. USA*, supra.

The polyadenylated RNA is used as the template for preparing a double-stranded cDNA copy using conventional techniques with one important modification. The first cDNA strand is synthesized using reverse transcriptase, an oligo-dT primer and the polyadenylated RNA as described by Baltimore, D. *Nature*, 226, 1209 (1970) and Temin, H. M. and Migutani, S., *Nature*, 226, 1212 (1970). The synthesis of the second strand of the cDNA is modified over the prior art. In the modified procedure, the first strand of cDNA is 3'-dC tailed using dCTP and terminal transferase in the method described by Roychoudhury, R., et al, *Nucl. Acids. Res.*, 3, 863 (1976). The second cDNA strand is then synthesized using reverse transcriptase, an oligo-dG primer and the first cDNA strand as described above. In the prior art procedure, the first cDNA strand is allowed to form a hairpin loop and self-prime the synthesis of the second strand. See, for example, Seeburg, P. H., et al, supra. This then required the digestion with S1 nuclease to open up the hairpin loop. This step generally leads to the loss of terminal DNA nucleotides. By using the modified procedure, the S1 digestion step is no longer needed and no terminal DNA nucleotides are lost.

The cDNA is now ready for insertion into an appropriate transfer vector using conventional techniques. For example, a synthetic nucleotide containing a recognition site for a particular restriction endonuclease can be blunt-end ligated to the cDNA. The cDNA and transfer vector are separately incubated with the restriction endonuclease and then annealed to form the transfer vector containing the cDNA. Alternatively, the cDNA can be dC tailed as described above and the transfer vector, after digestion with a restriction endonuclease such as Pst I, can be dG tailed. The dG-tailed transfer vector and dC tailed cDNA are then annealed to form the transfer vector containing the cDNA. The transfer vector containing the cDNA is then used to transform a suitable host, such as *E. coli* $\chi 1776$, as described by Seeburg, P. H., et al, supra. Colonies are selected for tetracycline resistance. Selected colonies are screened by conventional techniques. These may include (1) removing the cDNA by an appropriate restriction endonuclease and analyzing it by electrohoresis and hybridization (Southern, E. M., et al, *J. Mol. Biol.*, 98, 503 (1975); (2) replica-plating as described by Grunstein, M. and Hogness, D. S., *Proc. Nat. Acad. Sci. USA*, 72, 3961 (1975) and hybridizing with an appropriate probe; or (3) examining colonies directly for expression by radioimmunoassay or other techniques.

DNA coding for prolactin can be prepared from the insert coding for preprolactin. The DNA coding for preprolactin is removed by an appropriate restriction endonuclease. For example, if the cDNA is inserted in the Pst I site of the plasmid pBR322, the cDNA insert can be removed by partial digestion with Pst I. The cDNA insert is then modified by removal of nucleotides on the 5' end of the preprolactin coding sequence to yield a modified insert having a coding sequence for prolactin. This can be done either by controlled digestion of the 3' end of the insert using 3' exonuclease or T4 DNA polymerase or by the combination of restriction endonuclease cleavage at a point to the 3' side of the desired starting point and chemical synthesis to restore that portion of the desired sequence removed. For further details of these procedures, see copending application Ser. No. 125,878, filed Feb. 25, 1980, incorporated herein by reference.

One method for obtaining a cDNA coding for human prolactin is as follows. The cDNA insert for preprolactin is removed by partial digestion with Pst I and purified by preparative gel electrophoresis. The insert is then subjected to partial digestion with HaeIII which removes the nucleotides coding for all but two of the amino acids of the signal peptide. The last two amino acids are removed by digestion with T4 DNA polymerase in the presence of dATP. This then produces a new cDNA insert which codes for human prolactin. This cDNA can then be inserted into an appropriate transfer vector as described above.

One method for obtaining a cDNA coding for rat prolactin is as follows. The cDNA insert is removed as described above. The insert is then subjected to partial digestion with Mn1 I which removes all of the nucleotides of the signal peptide and the first twelve amino acids of the prolactin sequence. A sequence coding for the first twelve amino acids is synthesized by the phosphotriester method as described by Itakura, K., et al, *J. Biol. Chem.*, 250, 4592 (1975), Itakura, K., et al, *J. Am. Chem. Soc.*, 97, 7326 (1975) or by other suitable synthetic means. This sequence is then ligated to the modified cDNA insert to produce a new insert coding for rat prolactin. This cDNa is then inserted into an appropriate transfer vector as described above.

The cloned DNA is expressed in bacteria to yield either a fusion protein comprising the prolactin coded by the inserted sequence, or the prolactin itself. Several possible techniques are available as options, and may include (a) modification of the coding sequences to provide an exact desired translational starting point; (b) selection or construction of an optimal expression vector; (c) post-translational processing, either by exploiting in vivo processing activity of the host or by in vitro chemical means; and (d) direct expression.

When a fusion protein is expressed, modification of the cloned nucleotide sequence will generally be unnecessary as long as the resulting sequence permits translation of the insert in the correct reading frame and no stop codons intervene before the initial codon of the inserted sequence.

Preprolactin or prolactin is expressed as a fusion protein by insertion of the cDNA into appropriate sites within expressed operons (expression vectors) including for example the Pst I site in the β-lactamase gene of pBR322 (Villa-Komaroff, L., et al, *Proc. Nat. Acad. Sci. USA*, 75, 3727 (1978) and Seeburg, P., et al, *Nature*, 274, 795 (1978)), the EcoRI site of pBR322 carrying the lac control region and coding sequence for β-galactosidase (Itakura, K., et al, supra) or the HindIII site of the trpD gene of plasmid ptrpED50 (Martial, J., et al., *Science* 205: 602 (1979)). Modifications of sequence length by one or two nucleotides in order to achieve correct reading frame phase are well known in the art. Insertions at the Pst I site of pBR322, with the aid of the tailing procedure, occur in correct orientation and reading frame with a probability of 1/6.

Preprolactin or prolactin is prepared from a fusion protein susceptible of specific cleavage in vitro. The cloned nucleotide sequence is modified to code for amino acid sequences providing specificity for a proteolytic enzyme. A useful sequence is AspAspAspAspLys, cleaved preferentially by the enzyme enterokinase, as described in copending application Ser. No. 125,878. As described therein, a linking nucleotide sequence coding for the foregoing amino acid sequence is inserted adjacent the nucleotide sequence coding for the amino terminus of preprolactin.

Such insertion requires modification of the original cDNA insert, by removal of nucleotides on the 5' end of the preprolactin coding sequence. This is accomplished either by controlled digestion of the 3' end of the insert using 3' exonuclease or T4 DNA polymerase in the absence of nucleotides followed by S1 nuclease digestion or by the combination of restriction endonuclease cleavage at a point to the 3' side of the desired starting point and chemical synthesis to restore that portion of the desired sequence thus removed. By following these procedures, preferably using T4 DNA polymerase and S1 nuclease, the cDNA sequence coding for preprolactin and lacking the 5'-untranslated region is obtained. The linker nucleotide sequence coding for the foregoing amino acid sequence is blunt-end ligated to the cDNA using DNA ligase as described by Valenzuela, et al, *Nature*, 280, 815 (1979). The modified cDNA sequence is inserted into a fusion protein expression vector as previously described. Host bacteria, *E. coli* HB101, RR1, $\chi$1776 or other bacteria are transformed by the recombinant vectors bearing the inserted preprolactin coding region. Transformants are selected for resistance to ampicillin. Transformants are then grown under conditions suitable for expression of the fusion protein, After expression of the fusion protein, the preprolactin is cleaved out by enzymatic hydrolysis using enterokinase.

By the use of appropriate expression transfer vectors, the preprolactin or prolactin of the present invention is expressed directly, i.e., not fused to any procaryotic protein. Chang, A. C. Y., et al, *Proc. Nat. Acad. Sci. USA*, 77, 1442 (1980) have reported that they obtained direct expression of mouse dihydrofolate reductase (DHFR). The mouse DHFR coding sequence had been dC-tailed and inserted into the dG-tailed, Pst I site of pBR322. The authors found that transformed bacteria synthesized a protein having enzymatic properties, immunological reactivity and molecular size of the mouse DHFR. They also found that the cDNA for DHFR was in a different translation reading frame from the bacterial β-lactamase gene into which it had been inserted. These findings implied that translation was re-initiated at the start codon for the mouse DHFR under these circumstances, i.e., method of insertion, to produce mouse DHFR directly and not as part of a fusion protein.

The underlying principle of another form of direct expression is that the inserted DNA segment entirely replaces the coding segment normally transcrbied and translated by the bacterial control region. The essential component of the control region to be preserved is termed the expression unit, which includes a promoter and a ribosomal binding site capable of acting in the host organism. It is not necessary to remove all of the nucleotides coding for the host portion of the fusion protein. The relationship between the ribosomal binding site and the start codon (AUG) is such that the start codon may be located anywhere within 3–11 nucleotides of the ribosomal binding site. Shine, J., et al *Proc. Nat. Acad. Sci. USA*, 71, 1342 (1974) and Steitz, J., et al, *Proc. Nat. Acad. Sci. USA*, 72, 4734 (1975). In this 3–11 nucleotide region, the first AUG to be encountered sets the reading frame for translation. In the case of ptrpE30, derived from ptrpED50 described supra and containing the operator, promoter, leader, attenuator and ribosome binding sequences of the tryptophan operon together with the nucleotide sequence coding for seven amino acids of the trp E protein followed by a HindIII site, the removal of a minimum of 23–29 nucleotides from the HindIII site provides a site for insertion of the cDNA insert under tryptophan operon control.

For the direct expression of preprolactin, the original cDNA insert is modified as described above to remove the 5' untranslated region. A vector for direct expression can be constructed by modification of ptrpE30 by removing 23–29 nucleotides using T4 DNA polymerase and S1 nuclease as described above. A linker nucleotide sequence containing the restriction sequence for Bam HI endonuclease is blunt-end ligated to both the modified cDNA insert and the modified ptrpE30 by the procedure of Valenzuela, et al, supra. This is done to facilitate insertion which is performed essentially as described by Ullrich, A., et al, *Science*, 196, 1313 (1977). Host bacteria *E. coli* HB101, RR1, $\chi$1776 or other bacteria are transformed by the recombinant vectors bearing the inserted preprolactin coding region. Transformants are selected for resistance to ampicillin and then grown under conditions suitable for expression of preprolactin. Prolactin can also be expressed directly by following the procedure described in Goeddel, D. V., et al, *Nature*, 281, 544 (1979). Alternatively, a linker nucleotide sequence containing the Bam HI site and the start codon (ATG) can be blunt-end ligated to the cDNA coding for prolactin. This modified cDNA is then inserted into the modified ptrpE30 as described above.

Preprolactin is converted to prolactin by removal of the N-terminal sequence of hydrophobic amino acids that comprise the signal peptide. In vitro removal of the signal peptide might be carried out by treating the protein extracted from transformed, induced cells with a preparation of "rough" microsomes as described by Jackson, R. C. and Blobel, G., *Proc. Nat. Acad. Sci. USA,* 74, 5598 (1977). In vivo removal of the signal peptide may occur during direct bacterial expression of the preprolactin coding sequence. Bacterial and mammalian signal peptides share sequence similarities. Proteins having mammalian signal peptides may be processed by bacterial cells resulting in excretion of prolactin into the periplasmic space or into the medium. Talmadge, K., et al, *Proc. Nat. Acad. Sci. USA,* 77, 3369 (1980) have shown that rat proinsulin having a signal sequence, either bacterial or eucaryotic, is transported into the periplasmic space. Talmadge, K., et al, *Proc. Nat. Acad. Sci. USA,* 77, 3988 (1980) have shown that a bacterial peptidase cleaves away the eucaryotic signal sequence during transport into the periplasmic space of rat preproinsulin.

Proprolactin and prolactin synthesized as described are purified by techniques well known in the art, including, for example, gel filtration, ion exchange chromatography, affinity chromatography and differential solubility techniques.

The details of the present invention will be further described by the following examples. In these examples, digestions with restriction endonucleases were carried out under conditions optimized for each enzyme. Restriction endonucleases, their nomenclature and site specificity, have been described in detail by Roberts, R., *Crit. Rev. Biochem.,* 4, 123 (1976). Enzymes were obtained commercially (New England BioLabs, Cambridge, Mass.) and optimal conditions according to supplier's recommendations were employed unless noted otherwise. Reverse transcriptase was provided by Dr. J. Beard, Life Sciences, Inc., St. Petersburg, Fla. The use of reverse transcriptase and suitable reaction conditions have been described previously by Seeburg, P. H., et al, *Nature,* 276, 795 (1978); Seeburg, P. H., et al, supra; and Shine, J., et al, supra. T4 DNA polymerase was obtained from New England BioLabs. Micrococcal S1 nuclease was obtained from Miles Laboratories, Elkhart, Ind. The use of S1 nuclease and suitable reaction conditions have been previously described by Ullrich, A., et al, supra. Terminal deoxynucleotide transferase was obtained from Enzo Biochemicals, New York, N.Y. The use of this enzyme and suitable reaction conditions have been previously described by Roychoudhury, et al, supra.

EXAMPLE 1

Female rats are anesthetized and their medial basal hypothalami destroyed by the procedure described by Cheung, C. Y. and Weiner, R. I., *Endocrinology,* 99, 914 (1976). At the same time, 40 mm silastic capsules filled with 17β-estradiol were implanted subcutaneously. The hypothalamic ablation and estrogen treatment have been shown to increase circulating prolactin concentrations. Twenty-three days later, the rats were killed and the pituitaries removed.

The RNA was extracted from the pituitaries as follows. The pituitaries were homogenized in a guanidine thiocyanate solution (Chirgwin, J. M., et al, *Biochem.,* 18, 5294 (1979)). After homogenization, N-lauryl sarcosine and CsCl were added to the mixture to a final concentration of 2% and 0.35 g/ml respectively, and the resulting mixture was heated for two minutes at 65° C. This solution was then layered over a cushion of 5.7M CsCl and 1 mM EDTA and centrifuged in an SW 40 rotor at 32,000 rpm for 24 hours at 20° C. The pellets were dissolved in 10 mM Tris HCl, pH 7.5, 1 mM EDTA and 1% N-lauryl sarcosine, extracted with phenol and chloroform and precipitated with ethanol in the presence of 0.3M sodium acetate. Polyadenylated RNA was purified using oligo-dT-cellulose affinity chromatography as described by Aviv, H., et al, *Proc. Nat. Acad. Sci. USA,* 69, 1408 (1972).

The polyadenylated RNA was translated in a wheat germ cell-free system in the presence of [$^{35}$S] methionine, ad described by Martial, J. A., et al, *Proc. Nat. Acad. Sci. USA,* 74, 1816 (1977). Preprolactin synthesized in this system was immune-precipitated with rabbit antiserum to rat prolactin and the Cowan strain of *Staphylococcus aureus* as described by Martial, J. A., et al, supra. The $^{35}$S-proteins were electrophoresed on 12.5% SDS slab polyacrylamide gels, Laemmli, U. K., *Nature,* 227, 680 (1970). The gels were fixed, dried and exposed to X-ray film. This analysis indicated that mRNA coding for rat preprolactin represented about 80% of the total pituitary mRNA.

3 μg of single-stranded cDNA was made from 21 μg of polyadenylated RNA using reverse transcriptase as described by Seeburg, et al, supra, except that the reaction mixture was incubated for 75 minutes. RNA was removed by alkaline hydrolysis. The single-stranded cDNA was extracted with phenol and chloroform, chromatographed over G-50 Sephadex (trademark, Pharmacia, Inc., Uppsala, Sweden) and ethanol-precipitated. The single-stranded cDNA was 3'-dCMP-tailed (Roychoudhury, et al, supra) in 130 μl reaction mixture containing 140 mM potassium cacodylate, 30 mM Tris base (final pH 6.9), 100 μM dithiothreitol, 1 mM CoCl$_2$, 50 μM dCTP, 6.2 pM [α-$^{32}$P]dCTP (sp. Act. 300 Ci/mmole) and 28 units of terminal deoxynucleotide transferase. The reaction was incubated at 37° C. for 24 minutes and was monitored by incorporation of radioactivity precipitated on DE81 paper. The reaction was stopped with phenol and chloroform extraction after an estimated 80 dCMPs were added. The DNA was fractionated using G-50 Sephadex and ethanol precipitated. Oligo-(dG)$_{12-18}$ was used to prime synthesis of the second strand cDNA under conditions identical with the first strand synthesis except that only cold nucleoside triphosphates were present. Reaction was in 150 μl with 40 units of reverse transcriptase for 90 minutes at 42° C. The reaction was terminated with phenol and chloroform extraction. 1.9 μg of double-stranded cDNA was obtained after G-50 Sephadex chromatography and ethanol precipitation. FIG. 1 illustrates the method of preparing the reverse transcript as described above. The double-stranded cDNA was 3'dCMP-tailed in 50 μl of the previously described buffer with 500 pmole of dCTP/3'-end. The reaction was terminated with phenol and chloroform extraction after 15 dCMPs had been added to each end as estimated by incorporation of label. The cDNA was fractionated on G-50 Sephadex and ethanol-preciptated with 1 g of Torula RNA used as carrier.

Plasmid pBR322 was cleaved by Pst I endonuclease and tailed with dGMP by the previously described tailing reaction except that dGTP was used instead of dCTP and no radioactive label was present. Approximately 16 dGMPs/end were added by the reaction. 50 ng of the dG-tailed, Pst I cleaved pBR322 and 50 ng of the dC-tailed, double-stranded cDNA were annealed in 100 μl of a mixture containing 10 mM Tris HCl, pH 7.8, 1 mM EDTA and 100 mM NaCl. The mixture was heated at 80° C. for a few minutes, allowed to cool gradually to 42° C., incubated overnight at 42° C. and then cooled gradually to 4° C. Transformation of *E. coli* χ1776 with the plasmid preparation was carried out as described by Seeburg et al, supra (1977). Transformed colonies were selected for tetracycline resistance. To screen with a labelled probe, recombinant colonies were replica-plated onto Whatman 540 paper, lysed in situ and prepared for hybridization as described by Grunstein, et al, supra. The filters were hybridized to a $^{32}$P labelled cDNA probe synthesized from the prolactin-enriched polyadenylated RNA. Plasmids were isolated from the positive colonies, cleaved with Pst I and analyzed by agarose gel and Southern hybridization (Southern, supra) using a nick-translated plasmid containing a 486 base pair insert coding for a portion of rat preprolactin prepared according to Cooke, N. E., et al, *J. Biol. Chem.*, 255, 6502 (1980). The nick-translated probe was prepared as described by Maniatis, R., et al, *Proc. Nat. Acad. Sci. USA*, 72, 1184 (1975). 25 colonies were detected by hybridization of the cDNA probe. Only one of these contained a cDNA insert greater than 800 base pairs in length, the size expected for the full length rat preprolactin cDNA, which also hybridized with the 486 base pair probe. The insert was 823 base pairs in length and the plasmid was designated p-rPrl.

EXAMPLE 2

Synthesis of human preprolactin cDNA.

Human prolactin secreting tumors were obtained after surgical removal. The RNA was extracted from the tumors by following the procedure described in Example 1. The analysis of the polyadenylated RNA indicated that mRNA coding for human preprolactin represented the majority of the total tumor RNA. Double-stranded cDNA was prepared and inserted in pBR322 as described in Example 1. *E. coli* χ1776 was transformed and recombinant colonies selected, screened and analyzed as described in Example 1. An insert of 835 base pairs in length was obtained and the plasmid was designated p-hPrl.

EXAMPLE 3

Sequence analysis of the cDNA.

The deoxynucleotide sequences of p-rPrl and p-hPrl were analyzed by the method of Maxam, A. M. and Gilbert, W., *Proc. Nat. Acad. Sci. USA*, 74, 560 (1977). The sequence for the insert of p-rPrl is shown in FIG. 2 and the sequence for the insert of p-hPrl is shown in FIG. 3, together with the corresponding predicted amino acid sequences coded by the "sense" strands, i.e., the strands corresponding in sequence to the respective mRNAs. The correct reading frame is recognized by the lack of termination codons over a substantial portion of the inserts. The amino acid positions are numbered beginning with the amino-terminal amino acid of rat or human prolactin and proceeding in the positive direction to the carboxy terminal end and in the negative direction to the first AUG codon, presumed to be the point of translation initiation. The sequences suggest, in common with many other hormones, the synthesis of prolactin involves posttranslational processing. The translation of prolactin mRNA yields a precursor, preprolactin, containing a signal peptide which may be released during the transit into the endoplasmic reticulum.

EXAMPLE 4

Expression of rat or human prolactin.

Rat or human prolactin can be expressed by any of the methods described above. For purposes of illustration only, production of human prolactin by direct expression will be described. It is understood that rat prolactin can be prepared in the same manner and that rat or human prolactin can be prepared by any of the other described methods.

(A) Example 2 describes the preparation of p-hPrl containing the coding sequence for human prolactin. The sequence had been dC-tailed and inserted into the dG-tailed, Pst I site of pBR322. This plasmid was utilized to transform *E. coli* RR1. In this experiment, *E. coli* RR1 containing pBR322 was used as the control. *E. coli* RR1/p-hPrl and *E. coli* RR1/pBR322 were grown in nutrient broth and collected by centrifugation. The cells were frozen, thawed, resuspended and lysed. Cell debris was removed by centrifugation and the supernatants were frozen. The supernatants were thawed, dialyzed and centrifuged. The resulting supernatants were lyophilized. The lyophilizate was suspended in 3 ml of 50 mM ammonium bicarbonate and chromatographed over G-100 Sephadex (trademark, Pharmacia, Inc., Uppsala, Sweden) which had been standardized with blue dextran, β-mercaptoethanol and $^{125}$I-human prolactin. 30 drop fractions were collected and assayed for immunological activity and biological activity. The former was performed by conducting radioimmunoassay for human prolactin and the latter by conducting a receptor assay, i.e., binding human prolactin to its receptor. The control did not have a protein peak which corresponded to the $^{125}$I-human prolactin peak and none of the fractions contained any immunological or biological activity. The sample obtained from *E. coli* RR1/p-hPrl had a peak of radioimmune activity which corresponded to the $^{125}$I-human prolactin peak. The fractions from this peak are examined for biological activity. The fractions of this peak have biological activity in the receptor assay.

(B) In another example of direct expression of human prolactin the insert DNA is first separated from p-hPrl by partial Pst I endonuclease digestion and purified by preparative gel electrophoresis. A 15 μg sample of purified insert DNA is then modified by suspending the DNA in water to which is added a concentrated solution of salts such that the final composition comprises 70 mM Tris, pH 8.8, 70 mM MgCl$_2$, 10 mM dithiothreitol, 50 mM dTTP and 13.75 units of T4 DNA polymerase in a total volume of 250 μl. The reaction mixture is incubated at 37° C. and then the enzyme is inactivated by heat treatment at 65° C. for five minutes. This process is repeated twice more, once in which dGTP is used in place of dTTP and finally in which dTTP is again used. The treated DNA is recovered by ethanol precipitation. Digestion with S1 nuclease to provide blunt ends is carried out as described by Ullrich, A., et al, supra. This procedure is designed to produce a DNA molecule terminated at the start codon at the position numbered −28. Such molecules will be translated when inserted in an expression vector having an insertion site about 3–11 nucleotides from the ribosome binding site sequence of an expression unit.

A vector for direct expression is constructed by modification of the plasmid ptrpE30 by the removal of 23-29 nucleotides using T4 DNA polymerase and S1 nuclease as described above.

The modified insert and the modified expression vector are provided with a specific linker having the sequence 5'-CCGGATCCGG-3' on one strand and its complementary sequence on the other by blunt-end ligation using DNA ligase as described by Valenzuela, supra. The linkers provide restriction sites sensitive to Bam HI endonuclease which are employed to facilitate insertion. Insertion is accomplished by following the procedure of Ullrich et al, supra. Host bacteria $E.$ $coli$ HB101 or $E.$ $coli$ $\chi$1776 are transformed by the recombinant vectors bearing the inserted modified preprolactin coding region and transformants are selected for resistance to ampicillin. A single transformant designated ptrpE30/phP is selected for further analysis.

Bacterial cells transformed by ptrpE30/phP are grown in a standard minimal medium (M9) supplemented with Leu, Pro, vitamin B1 and amplicillin at 37° C. In early log phase, the trp operon is induced by the addition of $\beta$-indolylacrylic acid (30 $\mu$g/ml medium). Control cultures are left uninduced. After three more hours of growth, 1.5 ml of cells are radioactively labeled by the addition of 20 $\mu$Ci of $^{35}$S-L-Met and incubated for ten minutes. The cells are collected by centrifugation, washed and resuspended in 250 $\mu$l of buffer containing 10% (v/v) glycerol 5% (v/v) $\beta$-mercaptoethanol and 2.3% (w/v) SDS in 0.0625M Tris pH 6.8. The suspension is boiled for five minutes, then applied to a 10% (w/v) SDS-polyacrylamide gel and fractionated by electrophoresis. The protein bands are visualized by autoradiography. The results show the existence of a new protein band of about 26,000 daltons not observed in the uninduced or non-transformed cultures.

The human preprolactin is purified by conventional techniques including, for example, gel filtration, ion exchange chromatography, affinity chromatography and differential solubility techniques. Preprolactin is converted to prolactin by following the procedure described by Jackson, et al, supra.

While the invention has been described in connection with specific embodiments thereof, it will be understood that it is capable of further modifications and can be utilized to prepare prolactin from other animal sources for veterinary purposes. This application is intended to cover any variations, uses or adaptations of the invention following, in general, the principles of the invention and including such departures from the present disclosure as come within known and customary practice within the art to which the invention pertains.

The plasmid p-hPrl transformed into $E.$ $coli$ $\chi$1776 was deposited with the American Type Culture Collection, 12301 Parklawn Drive, Rockville, Md. 20852, and given Accession No. 31721. The plasmid p-rPrl transformed into $E.$ $coli$ $\chi$1776 was deposited with the American Type Culture Collection 18 Sept. 1980 and has ATCC Accession No. 31722. The deposits identified by Accession Nos. 31721 and 31722 are cross-referenced to Deposit Nos. 40028 and 40029, respectively.

FIG. 1

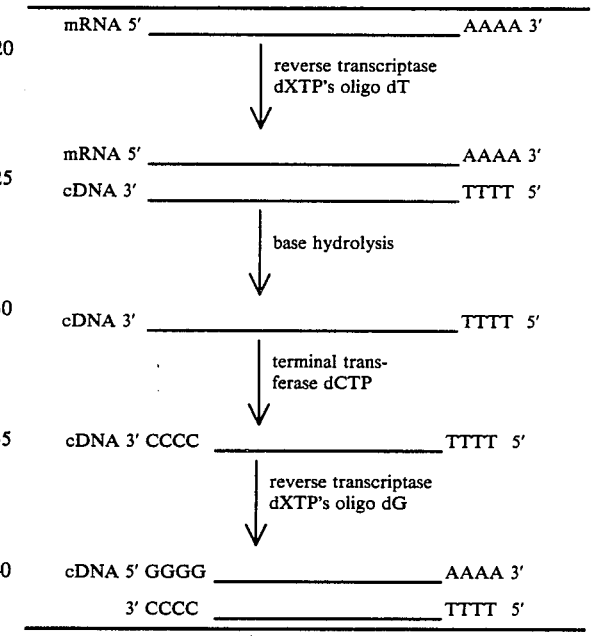

FIG. 2

RAT PROLACTIN

AGTGGTTCTCTTAGGACTTCTTGGGGAAGTGTGGTCCAGTGGTCATCACC

| | | | | | | | | | -28 | | | | | | | | | -20 | |
|---|---|---|---|---|---|---|---|---|---|---|---|---|---|---|---|---|---|---|---|
| Leu | Leu | Leu | Met | Met | Ser | Asn | Ser | Gln | Met | Asn | Ser | Ala | Arg | Lys | Gly | Thr |
| CTC | CTG | CTG | ATG | ATG | TCA | AAC | AGC | CAG | ATG | AAC | TCA | GCC | CGG | AAA | GGG | ACA |

| | | -10 | | | | | | | | | | | 1 | | | | | | |
|---|---|---|---|---|---|---|---|---|---|---|---|---|---|---|---|---|---|---|---|
| Leu | Cys | Leu | Pro | Thr | Leu | Asn | Leu | Leu | Phe | Cys | Gln | Thr | Val | Pro | Val | Cys | Ser | Gly | Gly |
| CTC | TGC | CTG | CCG | ACA | CTG | AAC | CTT | CTG | TTC | TGC | CAA | ACC | GTG | CCA | GTC | TGT | TCT | GGT | GGC |

| | | | 10 | | | | | | | 20 | | | | | | | | | 30 |
|---|---|---|---|---|---|---|---|---|---|---|---|---|---|---|---|---|---|---|---|
| Asp | Cys | Gln | Met | Asp | Phe | Ile | Glu | Leu | Phe | Val | Arg | Val | Val | Met | Leu | Ser | His | Thr | Tyr |
| GAC | TGC | CAG | ATG | GAT | TTT | ATT | GAA | CTG | TTT | GTG | CCT | GTC | ATG | CGT | CTG | TCT | CAC | ACC | TAT |

| | | 40 | | | | | | | | | | | | | | | 50 | | |
|---|---|---|---|---|---|---|---|---|---|---|---|---|---|---|---|---|---|---|---|
| THR | Asp | Met | Ala | Phe | Asp | Tyr | Gln | Val | Glu | Asp | Leu | His | Tyr | Ile | Ala | Ala | Leu | Asn | Asp |
| ACA | GAT | ATG | GCT | TTT | GAT | TAT | CAG | GTC | GAA | GAC | CTA | CAC | TAC | ATC | GCC | GCC | CTG | AAT | GAC |

| | | 60 | | | | | | | 70 | | | | | | | | | | |
|---|---|---|---|---|---|---|---|---|---|---|---|---|---|---|---|---|---|---|---|
| Cys | Pro | Thr | Ser | Leu | Pro | Thr | Pro | Glu | Asp | Lys | Glu | Gln | Ala | Phe | Gln | Lys | Pro | Val | Leu |
| TGC | CCC | ACT | TCT | CTA | CCT | ACT | GAA | GAC | AAG | AAG | CAA | GCC | TTT | CAA | AAG | CCG | GTC | CTT | TTG |

| 80 | | | | | | | | 90 | | | | | | | 100 | | | | |
|---|---|---|---|---|---|---|---|---|---|---|---|---|---|---|---|---|---|---|---|
| Asn | Leu | Ile | Leu | Ser | His | Val | Ser | Trp | Asn | Asp | Pro | Leu | Phe | Gln | Leu | Leu | Thr | Gly | Ile |
| AAC | CTG | ATC | CTC | AGT | CAC | GTG | TCC | TGG | AAT | GAC | CCT | CTG | TTT | CAA | CTA | CTA | ACT | GGA | ATC |

| | | 110 | | | | | | | | 120 | | | | | | | | | |
|---|---|---|---|---|---|---|---|---|---|---|---|---|---|---|---|---|---|---|---|
| His | Glu | Ala | Pro | Ile | Ile | Gly | Gln | Val | Ala | Lys | Ala | Leu | Ile | Asn | Lys | Arg | Leu | Trp | Gly |
| CAT | GAA | GCT | CCT | ATC | ATC | GGA | CAG | GTT | GCT | AAA | GCC | TTG | ATC | AAC | AAG | CGG | CTC | TGG | GAA |

| | | 130 | | | | | | | | 140 | | | | | | | | 150 | |
|---|---|---|---|---|---|---|---|---|---|---|---|---|---|---|---|---|---|---|---|
| Ile | Glu | Lys | Ile | Ile | Ala | Gly | Val | Glu | Ala | Lys | Ala | Glu | Asn | Tyr | Asn | Val | Arg | Gln | Leu |
| ATC | GAA | AAG | ATA | ATT | GCC | GCC | GTT | GAA | GCC | AAA | GCC | GAG | AAT | TAC | AAC | GTC | CGG | CAA | CTC |

| | | | 160 | | | | | | | 170 | | | | | | | | | |
|---|---|---|---|---|---|---|---|---|---|---|---|---|---|---|---|---|---|---|---|
| Pro | Ser | Leu | Glu | Asp | Ser | Lys | Lys | Arg | Asp | Ile | Arg | Cys | Leu | Arg | Asn | Asn | Lys | Arg | Arg |
| CCA | TCC | CTG | GAA | GAT | TCC | AAG | AAA | AGG | GAT | ATT | CGG | TGC | CTG | CGG | AAC | AAC | AAA | CGG | AGG |

| | 180 | | | | | | | 190 | | | | | | | | 197 | | | |
|---|---|---|---|---|---|---|---|---|---|---|---|---|---|---|---|---|---|---|---|
| Asp | Val | Lys | His | Tyr | Leu | Arg | Phe | Gln | Ile | Val | His | Cys | Asn | OC |
| GAT | GTT | AAG | CAC | TAT | CTC | AGG | TTC | CAA | ATT | GTC | CAT | TGC | AAC | TAA |

GCCTACATTCATTCCATGTACATCCGAGATGTTCTTCAAAGTTCTATTTGCATTACAACTTTCAGCACACATGCTTAAGA

FIG. 3
HUMAN PROLACTIN

|  | -28 Met ATG | Asn AAC | Ile ATC | Lys AAA | Gly GGA | Ser TCG | Pro CCA | Trp TGG | -20 Lys AAA | Pro CCC | Gly GGG | Ser TCC | Val GTG | Leu CTG | -10 Asn AAC | Leu CTG |
|---|---|---|---|---|---|---|---|---|---|---|---|---|---|---|---|---|
| Leu CTG | Cys TGC | Gln CAG | Ser AGC | Phe TTT | Ala GCC | Ala GCC | Pro CCC | 1 Leu TTG | Val GTC | Cys TGT | Ile ATC | Pro CCC | Gly GGC | Ala GCT | Ala GCT | Arg CGA |
| Asp GAC | Leu CTG | Asp GAC | Phe TTT | Arg CGC | Ala GCC | Ala GCC | Val GTC | Leu CTG | 10 Arg CGA | Ala GCT | Cys TGC | Gly GGG | Val GTG | Thr ACC | Leu CTT | Leu CTT |
| 40 Phe TTC | Lys AAA | Asp GAT | Thr ACC | Arg CGG | Tyr TAT | Thr ACC | His CAT | Gly GGC | Arg CGG | Ile ATC | Ser TCC | Ser TCA | Glu GAA | Phe TTC | Ser AGC | Glu GAA |
| Leu CTT | Ala GCC | Thr ACC | Pro CCC | Gly GGG | Lys AAG | Glu GAG | Gln CAA | Ala GCC | Gln CAA | Met ATG | Asn AAC | Ser AGC | Met ATG | 60 Thr ACT | Ser TCT | Ser TCC |
| Ser AGC | Ile ATA | Leu TTG | Arg CGA | Ser TCC | Gly GAA | Trp TGG | Asn AAT | Ser TCT | Ile ATT | Leu CTG | Leu CTG | His CAT | 80 Phe TTT | Arg CGT | Leu CTT | Ile ATA | Val GTC |
| Pro CCG | Glu GAG | Ala GCT | Ile ATC | Leu CTA | Ser TCC | Lys AAA | Val GTA | Gln CAA | Glu GAG | 100 Thr ACG | Glu GAA | Lys AAA | Tyr TAC | Pro CCT | Val GTC | Gly GGT | Glu GAA | Ala GCC |
| Leu CTG | Ile ATA | Ser AGC | Gln CAG | Val GTT | His CAT | Pro CCT | Thr ACC | Glu GAA | 120 Gln CAA | Glu GAG | Glu GAG | Thr ACC | Lys AAA | Tyr TAC | Arg CGT | Pro CCT | Leu CTT | 130 met ATG |
| Ser TCC | Leu CTG | Gln CAG | Met ATG | Ala GCT | 160 Asp GAT | Glu GAA | Ser TCT | Ser TCT | Arg CGC | Leu CTT | Leu CTT | Ile ATC | Ser AGC | Ser TCG | Trp TGG | 150 Cys TGC | Leu CTA | Leu CTT | Gly GGA | Pro CCA |
| Asp GAT | Ser TCA | 180 His CAT | Lys AAA | Ile ATC | Met ATG | Ile ATC | Asp GAC | Asn AAT | Tyr TAT | Leu CTC | Leu CTG | 190 Lys AAG | Cys TGC | Arg CGA | Ile ATC | His CAC | 170 Asn AAC | Leu CTG | Leu CTC | His CAC | Asn AAC | Asn AAC | Arg CGC | Arg AGG |
| Asp GAT | Ser TCA | 180 His CAT | Lys AAA | | | | | 190 Lys AAG | Cys TGC | Arg CGA | Ile ATC | His CAC | | | | | 199 Cys TGC | OC TAA |

GCCACATCCATTTCATCTATTTCTGAGAAGGTCCTTAATGATCCGTTCCATTGCAAGCTTCTCTTTAGTTGTATCTCTTTGAATCCATGC
TTGGGTGTAACAGGTCTCCTCTTAAAAATAAAAAACTGACTCGTTAGAGACATC

What is claimed is:

1. A recombinant, homogeneous cloned DNA which comprises a recombinant DNA sequence encoding rat prolactin of the amino acid sequence numbered 1 through 197 in FIG. 2.

2. A recombinant, homogeneous cloned DNA which comprises a recombinant DNA sequence encoding rat preprolactin of the amino acid sequence numbered −28 through 197 in FIG. 2.

3. A DNA transformer vector which comprises the DNA of claim 1 or 2.

4. A microorganism transformed by the transfer vector of claim 3.

5. The microorganism of claim 4 comprising *Escherichia coli* χ1776.

6. The transfer vector of claim 3 comprising p-rPrl.

7. A microorganism transformed by the transfer vector of claim 6.

8. The microorganism of claim 7, comprising *Escherichia coli* χ1776.

9. A DNA expression vector which comprises the DNA of claim 1 or 2.

10. A microorganism transformed by the expression vector of claim 9.

11. The microorganism of claim 10 comprising *Escherichia coli* χ1776 or *Escherichia coli* HB101.

12. A recombinant, homogeneous cloned DNA which comprises a recombinant DNA sequence encoding human prolactin of the amino acid sequence numbered 1 through 199 in FIG. 3.

13. A recombinant, homogeneous cloned DNA which comprises a recombinant DNA sequence encoding human preprolactin of the amino acid sequence numbered −28 through 199 in FIG. 3.

14. A DNA transfer vector which comprises the DNA of claim 12 or 13.

15. A microorganism transformed by the transfer vector of claim 14.

16. The microorganism of claim 15, comprising *Escherichia coli* χ1776.

17. The transfer vector of claim 14 comprising p-hPrl.

18. A microorganism transformed by the transfer vector of claim 17.

19. The microorganism of claim 18, comprising *Echerichia coli* χ1776.

20. A DNA expression vector which comprises the DNA of claim 12 or 13.

21. A microorganism transformed by the expression vector of claim 20.

22. The microorganism of claim 21 comprising *Escherichia coli* χ1776 or *Esherichia coli* HB101.

* * * * *